US011058735B2

(12) United States Patent
Sofer et al.

(10) Patent No.: US 11,058,735 B2
(45) Date of Patent: Jul. 13, 2021

(54) FORMULATIONS CONTAINING POMEGRANATE SEED OIL, ROSA CANINA FRUIT OIL AND INULA VISCOSA OLEORESIN OR EXTRACT

(71) Applicant: POMEGA, INC., San Anselmo, CA (US)

(72) Inventors: Tzeira Sofer, San Anselmo, CA (US); Tamara Meyer, Hoerdt (FR)

(73) Assignee: POMEGA, INC, San Anselmo, CA (US)

( * ) Notice: Subject to any disclaimer, the term of this patent is extended or adjusted under 35 U.S.C. 154(b) by 423 days.

(21) Appl. No.: 15/521,978

(22) PCT Filed: Nov. 2, 2015

(86) PCT No.: PCT/US2015/058682
§ 371 (c)(1),
(2) Date: Apr. 26, 2017

(87) PCT Pub. No.: WO2016/070194
PCT Pub. Date: May 6, 2016

(65) Prior Publication Data
US 2017/0333504 A1 Nov. 23, 2017

Related U.S. Application Data

(60) Provisional application No. 62/073,905, filed on Oct. 31, 2014.

(51) Int. Cl.
| | |
|---|---|
| *A61K 36/185* | (2006.01) |
| *A61K 9/00* | (2006.01) |
| *A61K 36/752* | (2006.01) |
| *A61K 36/28* | (2006.01) |
| *A61K 9/06* | (2006.01) |
| *A61K 47/44* | (2017.01) |
| *A61K 36/738* | (2006.01) |
| *A61K 31/202* | (2006.01) |
| *A61K 33/04* | (2006.01) |
| *A61K 33/30* | (2006.01) |
| *A61K 33/38* | (2006.01) |
| *A61K 35/644* | (2015.01) |
| *A61K 36/11* | (2006.01) |
| *A61K 36/23* | (2006.01) |
| *A61K 36/63* | (2006.01) |
| *A61K 36/73* | (2006.01) |
| *A61K 36/736* | (2006.01) |
| *A61K 36/76* | (2006.01) |
| *A61K 36/87* | (2006.01) |
| *A61K 36/886* | (2006.01) |
| *A61K 36/8998* | (2006.01) |

(52) U.S. Cl.
CPC .......... *A61K 36/185* (2013.01); *A61K 9/0014* (2013.01); *A61K 9/06* (2013.01); *A61K 31/202* (2013.01); *A61K 33/04* (2013.01); *A61K 33/30* (2013.01); *A61K 33/38* (2013.01); *A61K 35/644* (2013.01); *A61K 36/11* (2013.01); *A61K 36/23* (2013.01); *A61K 36/28* (2013.01); *A61K 36/63* (2013.01); *A61K 36/73* (2013.01); *A61K 36/736* (2013.01); *A61K 36/738* (2013.01); *A61K 36/752* (2013.01); *A61K 36/76* (2013.01); *A61K 36/87* (2013.01); *A61K 36/886* (2013.01); *A61K 36/8998* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 5,698,206 | A * | 12/1997 | Becker | A61K 8/9789 424/401 |
| 6,113,940 | A * | 9/2000 | Brooke | A61K 31/352 424/448 |
| 6,342,208 | B1 * | 1/2002 | Hyldgaard | A61K 8/06 424/400 |
| 8,263,140 | B1 | 9/2012 | Dreher | |
| 8,545,904 | B1 | 10/2013 | Morse | |
| 2004/0161524 | A1 | 8/2004 | Sakai et al. | |
| 2004/0185123 | A1* | 9/2004 | Mazzio | A61K 36/28 424/730 |
| 2005/0158258 | A1* | 7/2005 | Fisher | A61Q 19/08 424/63 |
| 2008/0166313 | A1 | 7/2008 | Jochim et al. | |
| 2009/0068255 | A1 | 3/2009 | Yu et al. | |
| 2010/0119463 | A1 | 5/2010 | Jacobs | |
| 2010/0267599 | A1* | 10/2010 | Lucka | A61K 8/922 510/139 |
| 2012/0244087 | A1 | 9/2012 | Trivedi et al. | |
| 2013/0064777 | A1 | 3/2013 | Tamarkin et al. | |
| 2014/0079819 | A1 | 3/2014 | Debaun | |

FOREIGN PATENT DOCUMENTS

| | | |
|---|---|---|
| DE | 202006019183 U1 | 4/2007 |
| JP | 2002-173405 A | 6/2002 |
| JP | 2006-104098 A | 4/2006 |
| JP | 2014-521703 A | 8/2014 |
| WO | 199805005 A1 | 11/1998 |
| WO | WO1998050005 A1 | 11/1998 |
| WO | 2005097187 A2 | 10/2005 |

(Continued)

OTHER PUBLICATIONS

Chrubasik, et al., Phytother. Res., 22:725. (Year: 2008).*

(Continued)

*Primary Examiner* — Michael Barker
(74) *Attorney, Agent, or Firm* — Hogan Lovells US LLP

(57) ABSTRACT

The invention relates, in general, to healing formulations containing pomegranate seed oil, *rosa canina* fruit oil, and inula viscosa oleoresin or extract. In some instances the formulations may also contain *citrus medica* vulgaris etrog oil or extract and other ingredients. The healing formulations are all natural, do not include any artificial preservatives and are safe and effective for treating certain skin disorders and conditions.

25 Claims, No Drawings

(56) References Cited

FOREIGN PATENT DOCUMENTS

| WO | 2005-117925 | A1 | | 12/2005 | |
| WO | WO-2005117925 | A1 | * | 12/2005 | ............. A61K 36/28 |
| WO | 2007004229 | A2 | | 1/2007 | |
| WO | 2009031153 | A2 | | 3/2009 | |
| WO | 2010089566 | A2 | | 8/2010 | |
| WO | 2012090194 | A | | 7/2012 | |
| WO | WO2012090194 | A2 | | 7/2012 | |

OTHER PUBLICATIONS

Truth in Aging (Review, https://www.truthinaging.com/review/pomega5-grenade-anti-rides-nourishing-cream+&cd=3&hl=en&ct=clnk&gl=US). (Year: 2012).*

Uncategory, "Citron Oil: Benefits, Uses, Properties, and Side Effects," htttps://uncategory.com/citron-oil. (Year: 2019).*

Bedel, et al., Indian J. Pharm. Sci., 79:328. (Year: 2017).*

S.R. Colby, Weeds, 15:20. (Year: 1967).*

Database WPI, Week 199218, Thomson Scientific, London, GB; An 1992-143609, XP002780454, & IL 80 329 A (Moraz Med Herbs Ltd) Mar. 29, 1992.

Supplemental European Search Report for European Patent Application No. 15855671.2 dated May 5, 2018.

International Search Report and Written Opinion for PCT/US2015/058682 dated Feb. 5, 2016.

Daily Revitalizing Concentrate,[online],Pomega, Inc.,2010 http://web.archve.orgThe Internet, URL,https://web.archive.org/web/20100912083024/https://www.pomega5.com/store/products .php?product=Daily—Revitalizing—Concentrate.

Nina Times [online, **-***, 2010, No. 12, [Search on Nov. 29, 2019], Internet, URL,https://www.ninapharm.co.jp/mb2/times12.pdf.

Tamura Hiroaki, et al., New Cosmetics Handbook, Oct. 30, 2006, p. 1 17, "1. Fat and oil".

Tamura Hiroaki, et al., New Cosmetics Handbook, Oct. 30, 2006, pp. 358 to 391, "14. Plant / seaweed extract".

Edited by Mitsui Takeo, New Cosmetics, Nanzando, Jan. 18, 2001, second edition, pp. 167 to 188, "6 Cosmetics and medicines".

Tubaro A et al.,Comparative topical anti-inflammatory activity of cannabinoids and cannabivarins,Fitoterapia,2010, vol. 81, No. 7,p. 816-819.

Tamura Hiroaki, et al., New Cosmetics Handbook, Oct. 30, 2006, p. 18 23, "2, Waxes," etc.

Development and application of new plant oleaginous bases having Obridged Yukohiro, lanolin properties, and the application for cosmetics, vol. 31, No. 11, pp.

Japanese Office Action dated Dec. 10, 2019 corresponding to Japanese Application No. 2017-542823.

International Search Report, dated Jul. 24, 2019, corresponding to PCT/US/2015/058682.

Yukihiro Ohashi, "Development and Application of New Plant Oleaginous Bases Having Lanolin Properties, and Application for Cosmetics," Fragrance Journal, Nov. 15, 2003, vol. 3 (11), 55 to 60.

Masahiro Sato, et al., A Study of Photo-Oxidization, Skin Irritancy, and Cytotoxicity of Triglycerides, Journal of Society of Cosmetic Chemists of Japan, 1986, vol. 20, No. 1, pp. 35 to 40.

Japanese Office Action dated Sep. 8, 2020, corresponding to Patent Application No. 2017-542823.

* cited by examiner

FORMULATIONS CONTAINING POMEGRANATE SEED OIL, ROSA CANINA FRUIT OIL AND INULA VISCOSA OLEORESIN OR EXTRACT

This application is a 371 national phase filing of PCT/US2015/058682, filed on Nov. 2, 2015, which claims priority to U.S. provisional application 62/073,905, filed on Oct. 31, 2014, the contents of both are herein incorporated by reference in their entireties.

BACKGROUND OF THE INVENTION

Field of the Invention

The invention relates, in general, to healing formulations containing pomegranate seed oil, *rosa canina* fruit oil, and inula viscosa oleoresin or extract. In some instances the formulations may also contain *citrus medica* vulgaris etrog oil or extract and other ingredients. The healing formulations are all natural, do not include any artificial preservatives and are safe and effective for treating certain skin disorders and conditions.

Background

The pomegranate tree, which is said to have flourished in the Garden of Eden, has been extensively used as a folk medicine in many cultures. In ancient Greek mythology, pomegranates are known as the "fruit of the dead," and in the ancient Hebrew tradition, pomegranates adorned the vestments of the high priest. The Babylonians regarded its seeds as an agent of resurrection, the Persians as conferring invincibility on the battlefield and for ancient Chinese it symbolized longevity and immortality.

Pomegranate fruit and its parts have been studied for their antiviral and antifungal effects. For example, U.S. Pat. No. 5,840,308 describes an antiviral and antifungal composition that includes a mixture of a ferrous salt and an extract of a plant including, among other things, pomegranate rind. U.S. Pat. No. 5,411,733 describes an antiviral agent containing a crude drug from, among other things, the root bark and fruit peel of pomegranate. U.S. Pat. Nos. 5,840.308 and 5,411,733 are expressly incorporated herein by reference in their entirety to more fully describe the state of the art.

Pomegranate seed oil can be extracted from dried seeds of the pomegranate fruit via any one of several known methods. Pomegranate seed oil is a botanical source for Omega-5 fatty acid, which is a conjugated unsaturated fatty acid. Fatty acids are central building blocks of life, and they help maintain the health of cell membranes, improve nutrient use and establish and control cellular metabolism. They also provide the raw materials that help in the control of blood pressure, blood clotting, inflammation, body temperature and other body functions. Fatty acids are obtained in their greatest quantities by the consumption of fat. Thus, although many people are encouraged to consume less fat in their diets, fat is still an important component of a healthy body, and the synthesis of fatty acids is essential to all organisms.

Fatty acids can be either saturated or unsaturated. Saturated fatty acids do not contain any double bonds. Saturated fatty acids form straight chains and, as a result, can be packed together very tightly, allowing living organisms to store chemical energy very densely. Unsaturated fatty acids are of similar form, except that one or more double bonds (i.e., "—CH=CH—") are part of the chain. In this regard, Omega 3, 5, 6 and 9 fatty acids are unsaturated.

The main substance in pomegranate oil is punicic acid (PA). Punicic acid (also known also as trichosanic acid), is a conjugated linolenic acid isomer containing cis-9, trans-11, cis-13 double bonds in the C18 carbon chain. In this context, U.S. patent application Ser. No. 11/039,419 discusses the use of punicic acid to enhance immune response and prevent metabolic disorders.

Punicic acid (PA) has 4 mechanisms of action. First, it is a powerful antioxidant approximately 10 times greater than that of grape seed extract. Second, PA is a conjugated linolenic acid (CLA). There is considerable interest in CLAs because they are anti-inflammatory, anti-plaque in blood vessels, and antitumor. Most CLAs come from animal sources. PA is the only medicinal oil that is a useable CLA that comes from a plant source. CLAs bind to receptors on the nucleus of cells that regulate the production of glucose transport channels. Therefore, CLA is important in the control of glucose transport at the cell surface. Third, PA has three double bonds in the 9 cis, 11 trans, and 13 cis, position. These double bonds bend the fatty acid chain in a way that resembles arachadonic acid. Arachadonic acid is powerful pro-inflammatory fatty acid that is the precursor of inflammatory prostaglandins that produce disease. PA inhibits the production of arachadonic acid and down regulates the production of prostaglandins and leukotrienes that cause disease without adverse effects like those caused by non-steroidal anti-inflammatory drugs (aspirin e.g.). Fourth, PA has a profound effect on the electromagnetic field. Field energy science is a relatively new area of medicine and technology. Pomegranate oil is being investigated as an anti-tumor drug, especially prostate cancer in males and breast cancer in females world wide. It is also being assessed as an anti-inflammatory drug in several immune complex disorders such as multiple sclerosis and systemic lupus erythematosis, and in cardiovascular disease in the prevention of arterial plaque that results in heart attacks.

Pomegranate seed oil also contains in addition to punicic acid, palmitic acid, stearic acid, oleic acid and linoleic acid.

The human body can produce all but two of the fatty acids it needs. The two fatty acids that cannot be produced by the human body are linoleic acid and alpha linoleic acid, which are widely distributed in plant and fish oils. Since they cannot be made in the body from other substrates and must instead be supplied in food, they are called essential fatty acids. Essential fatty acids are polyunsaturated fatty acids, and are the parent compounds of the Omega-3, 5 and 6 fatty acid series, respectively. As noted above, the seed oil from pomegranates is an unsaturated fatty acid (punicic acid) and constitutes between 60-86% of the oil of the pomegranate fruit. Punicic acid is known to have an extremely strong ability to resist the oxidizing, inflammation and destruction functions of the free radical of oxygen. As such, punicic acid may have wide application prospects in medicines and health protection, food and the cosmetics industry.

Pomegranate seed oil is absorbed into the human skin, and from there into body cells. Therefore, it can be used to treat certain skin disorders as either a stand alone product or when combined with the other ingredients. Given these unique properties, the pomegranate seed oil is an element or nanotechnology.

Personal care products must be functional, aesthetically pleasing and safe. When it comes to formulations to be used directly on skin, it is preferable that such products are not separated, have not broken down and do not contain bacteria or mold. To protect the integrity of cosmetics and toiletries, and to ensure consumer safety, commercially available cosmetics generally include preservative systems having artificial compounds, such as parabens.

Parabens are thought to be dangerous. Many companies in the personal care industry, therefore, have an interest in reducing reliance upon traditional preservative systems that include parabens. Given the current desire to develop safer, more natural products (i.e., those that minimize or eliminate dangerous ingredients, such as parabens), efforts are being made to develop new preservative systems capable of preserving formulations made primarily or exclusively of natural ingredients. Such systems and ingredients are notoriously difficult to preserve. In this regard, an ideal preservative is expected to be able to (i) eradicate a wide range of microorganisms, (ii) be effective at low concentrations, (iii) be water and/or oil insoluble, (iv) be stable under desired temperatures and PH conditions, (v) be colorless and odorless, (vi) not react with other ingredients to form colors or odors, (vii) be compatible with other ingredients and not alter their effectiveness, (viii) retain the shelf life for the life of the cosmetics and (ix) be safe to use.

Parabens may be substituted by botanical or other natural ingredients that have strong antioxidant and distinct disincentive anti-bacteria or antibiotics properties. The invention describes a mixture of ingredients to include a dosage of oils and oleoresins derived from pomegranate seeds, rose hip, and the Inula Viscosa shrub and in some instances the Etrog fruit (*citrus medicus* vulgaris etrog) to create a totally natural preservative environment. Previous studies have used pomegranate seed oil but the results have been disappointing. It is believed that this is because the pomegranate seed oil is unstable and is easily oxidized and becomes inactive when oxidized. The inventors of the present invention have provided compositions where the pomegranate seed oil, not only contains a large amount of punicic acid (80%) but is also to maintain the pomegranate seed oil in an unoxidized state using other natural ingredients. The compositions provided herein have proved to be stable for at least 24 months when kept out of direct sun and at a normal room temperature (less than 78° F.).

The etrog is a medium to large sized bumpy yellow skinned citrus having a very acidic flavor. Its skin can be used as a source for an extract and its seeds and skin can also be used to produce oil. The fruit itself plays a role in the Jewish Feast of the Tabernacles.

The Inula Viscosa is a sturdy perennial shrub that grows in the wild around the Mediterranean Basin. It is known for its antioxidant and anti-inflammatory properties and has been known to be used for centuries as a treatment, among others, for arthritis, wounds, ulcer, respiratory tracts infections, athlete's foot, hemorrhoids, blood pressure, diabetes, and gum disorder. The leaves of the plant can be boiled to create a medicinal potion, or they can be extracted to create an oleoresin.

SUMMARY OF THE INVENTION

There is provided composition, formulations, treatment regimens, methods of treatment and kits.

A healing composition useful in the healing or treatment of skin conditions wherein the composition comprises contain punica granatum oil (pomegranate seed oil) having about 80% punicic acid, *rosa canina* fruit oil, and inula viscosa oleoresin (or its extract), wherein the punica granatum oil is unoxidized is provided. It is believed that the use of these three ingredients, all containing CLAs work in synergy to provide better efficacy by increased absorbion and reduced oxidation of the punica granatum oil.

The healing composition may further comprise *citrus medica* vulgaris etrog oil (or its extract). The composition can be formulated into a solid wherein the 80% punicic acid is at 3-6%, the rasa canina oil is at 2-5%, the inula viscosa oleoresin is at 0.05-1.5% and the *citrus medica* vulgaris etrog oil is at 0.1-2%. This composition is useful as a healing bar used in cleansing of the skin. The healing bar may further comprise *Calendula officinalis* in joboba oil at 2-4%, *olea europea* (olive oil) at 1-3%, *butyrspermum parkii* butter (shea butter) at 2-5%, *aloe barbadensis* gel at 1.5-3.5%, sulfur at 0.75-4%, colloidal silver at 0.5-3%, *achillea millefolium* (common yarrow) at 0.5-2%; *equisetum arvense* (horsetail) at 0.5-2%, chamomile flower extract at 1-3% and zinc at 0.5-1.75%. The healing bar may further comprise *cannabis* oil at 0.05-1.5%.

Healing compositions of the invention may be formulated into a balm/occlusive dressing wherein the punica granatum oil (pomegranate seed oil) having about 80% punicic acid is at 5-9%; *rosa canina* oil (rose muscat)(rose hip) at 4-8%; and inula viscosa oleoresin extract at 0.04-0.2% and further comprises Calendula infused Jojoba oil at 50-67%. The composition may further comprising cera alba (beeswax) at 15-25% and vegetable lanolin (omega 3) as its base. The composition may further comprises *cannabis* oil at 2-4%.

Healing compositions may be formulated into a healing cream wherein the punica granatum oil (pomegranate seed oil) having about 80% punicic acid at 2-5%, *rosa canina* oil (rose muscat)(rose hip) at 2-4%, and inula viscosa oleoresin at 0.03-0.2% and may further comprises *butyrspermum parkii* butter (shea butter) at 3.0-6.0%, cera alba (bees wax) at 3.0-6.0%, *aloe barbadensis* leafjuice at 1.0-1.6%, prunus amygdalus dulcis oil (sweet almond oil) at 3.0-6.0%, *Vitis vinifera* seed oil (grape seed oil) at 2.0-4.0%, *Daucus carota* sativa root extract (wild carrot extract in olive oil) at 2.0-5.0%, sunflower seed oil at 0.1-0.3% and *Calendula officinalis* flower extract (marigold) infused jojoba oil at 8.5-14.5%.

The healing composition may be formulated into a healing cream wherein the punica granatum oil (pomegranate seed oil) having about 80% punicic acid at 4-8%, *rosa canina* oil (rose muscat)(rose hip) at 4-8%, and inula viscosa oleoresin at 0.03-0.3 and further comprises *Salix alba* bark extract (white willow bark) at 1.0-3.0%, chamomile flower extract at 1.5 to 3.0%, *Humulus lupulus* cone extract (common hop) at 1.0 to 2.0%, colloidal silver in water 1.0-2.0%, *citrus medica* vulgaris etrog fruit extract at 1-5% and *Hordeum vulgare* extract (common barley) at 1.5-3.5%, The healing cream composition may further comprising *butyrspermum parkii* butter (shea butter) at 2.5-5.0, cera alba (bees wax) at 2.0-5.0%, *aloe barbadensis* leaf juice at 1.0-3.0%, prunus amygdalus dulcis oil (sweet almond oil) at 3.0-7.0%, *Vitis vinifera* seed oil (grape seed oil) at 1.0-3.0%, *Daucus carota* sativa root extract (wild carrot extract in olive oil) at 3.0-6.0%, sunflower seed oil at 0.1-0.4% and *Calendula officinalis* flower extract (marigold) infused jojoba oil at 5.0-10%).

Compositions of the invention may be formulated into a Concentrated Repair Treatment ("CRT") wherein punica granatum oil (pomegranate seed oil) having about 80% punicic acid at 45-65%; Calendula infused Jojoba oil at 15-25%, and *rosa canina* oil (rose muscat)(rose hip) at 20-35%. The CRT may further comprise inula viscosa oleoresin oil or extract at 0.01-2% and/or *citrus medica* vulgaris etrog oil or extract at 0.01-2%, *olea europea* (olive oil) at 1-8% and/or tocopherol (vitamin E oil) at 0.5-1.5%.

Treatment regimens and methods of treatment using compositions of the invention are provided. For example, treatment regimens for treating a patient having had an injury or treatment that destroys or damages the epidermis, treating radiodermatitis, ectopic dermatitis, psoriasis, eczema, rosacea, acne, warts, or blisters, canker sores (in the mouth), Xerosis cutis, and treating patients post plastic surgery and post injection of fillers are provided.

Kits comprising compositions of the invention are also provided.

DETAILED DESCRIPTION OF THE INVENTION

The invention relates, in general, to compositions and treatment regimens where the compositions contain pomegranate seed oil, rose hip oil, and inula viscosa oleoresin (or its extract) and/or *citrus medica* vulgaris etrog oil (or its extract) for treating various skin conditions, addressing inflammation of the skin manifested as very dry skin or chronic dry skin, damaged skin and wounds. The invention also provides methods of treatment and kits containing products comprising the formulations. The compositions are all natural, do not include any artificial preservatives and are safe and effective for treating certain skin disorders and conditions.

Healing Compositions

Healing compositions of the invention comprise punica granatum oil (pomegranate seed oil) having about 80% punicic acid, *rosa canina* fruit oil/*rosa rubiginosa* (rose muscat or rose hip), and inula viscosa oleoresin (or its extract). Compositions of the invention may also contain other ingredients. In some instances the compositions may comprise *citrus medica* vulgaris etrog oil or its extract. *Citrus medica* vulgaris etrog oil or extract may be from, but is not limited to: *citrus medica* vulgaris peel oil (which is the volatile oil obtained from the peel of the cedrat, *citrus medica* 1. var. vulgaris, rutaceae); *citrus medica* vulgaris fruit extract (which is the an extract of the fruit of the cedrat, *citrus medica* 1. var. vulgaris, rutaceae); or *citrus medica* sarcodactylus callus extract (which the extract of the callus of *citrus medica* sarcodactylus grown in culture, rutaceae).

Healing compositions of the invention can be used in conjunction with a concentrated repair treatment ("CRT") or also referred to as "ampules" as the CRT is provided in ampules. CRT of the invention are described in more detail below. CRT/ampules of the invention are generally not used in conditions where the skin barrier (epidermis is damages or diminished). They are very beneficial when the skin is damaged but when still intact (such as in rosacea, scratches, or scars—these instances the damage to the skin is not as deep as with psoriasis or eczema with lesions). CRT/ampules of the invention are preferably only used once a day. CRT/ampules are also used in embodiments of the invention in maintenance regimens described herein.

The punica granatum oil is unoxidized as oxidation destroys the activity of the punicic acid. The punica granatum oil (pomegranate seed oil), *rosa canina* oil, inula viscosa oleoresin and *citrus medica* vulgaris etrog all contain CLAs. LCAs are conjugated linoleic acids (CLA) are a family of at least 28 isomers of linoleic acid that are found mostly in the meat and dairy products derived from ruminants. CLAs can be either cis- or trans-fats and the double bonds of CLAs are conjugated and separated by a single bond between them. However CLAs are also found in plant products. To date, it has not been possible to isolate CLAs from plant sources.

The compositions can be formulated into different products that are useful in treatment regimens and methods of treatment for various skin conditions and damage to the epidermis.

"Healing Bar"

A healing composition of the invention may be provided as a formulation that is useful for cleansing of the skin for various skin conditions that are often accompanied with inflammation, such as but not limited to eczema, ectopic dermatitis, psoriasis and radiodermatitis. The composition can be formulated into a solid and shaped like a bar or cake of soap. This formulation is referenced herein as "a healing bar." A healing bar of the invention comprises punica granatum oil (pomegranate seed oil) having about 80% punicic acid at 3-6% (percentages herein mean percent of the total composition), *rosa canina* oil at 2-5%, inula viscosa oleoresin at 0.05-1.5% and *citrus medica* vulgaris etrog oil at 0.1-2%. A healing bar composition may also comprise, in addition to the "active ingredients" provided above, *Calendula officinalis* in joboba oil at 2-4%, *olea europea* (olive oil) at 1-3%, *butyrspermum parkii* butter (shea butter) at 2-5%, *aloe barbadensis* gel at 1.5-3.5%, sulfur at 0.75-4%, colloidal silver at 0.5-3%, *achillea millefolium* (common yarrow) at 0.5-2%; *equisetum arvense* (horsetail) at 0.5-2%, chamomile flower extract at 1-3% and zinc at 0.5-1.75%. The base of the healing bar is preferably coconut and palm oil. The healing bar may consist essentially of or may consist of the aforementioned ingredients.

In certain embodiments, healing bars of the invention are as described above but they may additional comprise *Cannabis* oil at 0.05-1.5%. *Cannabis* oil is a thick, sticky, resinous substance made up of cannabinoids, such as THC and CBD, that is extracted from the *cannabis* plant (*cannabis* sativa or *cannabis* indica), Such healing bar is useful in the treatment regimen for acne, blisters, warts and cuts.

Balm or "Occlusive Dressing"

A healing composition of the invention may be provided as a composition that is useful as a balm or an "occlusive dressing" in treatment regimens and methods of treatment described herein. The balm or "occlusive dressing" comprises Calendula infused Jojoba oil at 50-67%, punica granatum oil (pomegranate seed oil) having about 80% punicic acid at 5-9%; *rosa canina* oil (rose muscat)(rose hip) at 4-8%; and inula viscosa oleoresin extract at 0.04-0.2%. An occlusive dressing composition may also comprise cera alba (beeswax) at 15-25% and vegetable lanolin (omega 3) as its base. An occlusive dressing may consist essentially of, or may consist of, the aforementioned ingredients.

In certain embodiments an occlusive dressing may further comprise *cannabis* oil at 2-4%. Such occlusive dressing is useful in the treatment regimen for acne, blisters, warts and canker sores.

Healing Cream 1

A healing composition of the invention may be provided as a formulation that is useful as a healing cream. A healing cream 1 formulation may comprise: punica granatum oil (pomegranate seed oil) having about 80% punicic acid at 2-5%, *rosa canina* oil (rose muscat)(rose hip) at 2-4%, and inula viscosa oleoresin at 0.03-0.2%. A healing cream formulation 1 may further comprise *butyrspermum parkii* butter (shea butter) at 3.0-6.0%, cera alba (bees wax) at 3.0-6.0%, *aloe barbadensis* leaf juice at 1.0-1.6%, prunus amygdalus dulcis oil (sweet almond oil) at 3.0-6.0%, *Vitis vinifera* seed oil (grape seed oil) at 2.0-4.0%, *Daucus carota* sativa root extract (wild carrot extract in olive oil) at 2.0-5.0%, sunflower seed oil at 0.1-0.3% and *Calendula officinalis* flower extract (marigold) infused joboba oil at 8.5-14.5%. A healing cream formulation 1 may consist essentially of the aforementioned ingredients and can have oil-in-water emulsifiers and emulsion stabilization agents, natural preservatives, viscosity enhancers, and water as necessary.

Healing Cream 2

A healing composition of the invention may be provided as a formulation that is useful as a healing cream. A healing cream 2 formulation may comprise: punica granatum oil (pomegranate seed oil) having about 80% punicic acid at 4-8%, *rosa canina* oil (rose muscat)(rose hip) at 4-8%, and inula viscosa oleoresin at 0.03-0.3. A healing cream 2 formulation may further comprise *Salix alba* bark extract (white willow bark) at 1.0-3.0%, chamomile flower extract at 1.5 to 3.0%, *Humulus lupulus* cone extract (common hop) at 1.0 to 2.0%, colloidal silver in water 1.0-2.0%, *citrus medica* vulgaris etrog fruit extract at 1-5% and *Hordeum vulgare* extract (common barley) at 1.5-3.5%. A healing cream formulation 2 may further comprise *butyrspermum parkii* butter (shea butter) at 2.5-5.0, cera alba (bees wax) at 2.0-5.0%, *aloe barbadensis* leaf juice at 1.0-3.0%, prunus amygdalus dulcis oil (sweet almond oil) at 3.0-7.0%, *Vitis vinifera* seed oil (grape seed oil) at 1.0-3.0%, *Daucus carota* saliva root extract (wild carrot extract in olive oil) at 3.0-6.0%, sunflower seed oil at 0.1-0.4% and *Calendula officinalis* flower extract (marigold) infused joboba oil at 5.0-10%). A healing cream formulation 2 may consist essentially of the aforementioned ingredient and can have oil-in-water emulsifiers and emulsion stabilization agents, natural preservatives, viscosity enhancers, and water as necessary.

Concentrated Repair Treatment ("CRT")/Ampules

A composition is provided for use as a concentrated repair treatment ("CRT"). A CRT/ampule may comprise punica granatum oil (pomegranate seed oil) having about 80% punicic acid at 45-65%; Calendula infused Jojoba oil at 15-25%, and *rosa canina* oil (rose muscat)(rose hip) at 20-35%. A CRT/ampule may consist essentially of, or may consist of the aforementioned ingredients. In certain embodiments the CRT/ampule may also comprise and inula viscosa oleoresin oil or extract at 0.01-2% and/or *citrus medica* vulgaris etrog oil or extract at 0.01-2%. A CRT/ampule may consist essentially of or may consist of the aforementioned ingredients. A CRT/ampule of the invention may further comprise *olea europea* (olive oil) at 1-8% and/or tocopherol (vitamin E oil) at 0.5-1.5%. In some embodiments almond oil may be present at 10-15%. In certain embodiments the CRT does not contain additional botanical essential oils such as Vevain oil, rosewood oil, lemon oil, and/or grapefruit oil.

In certain instances as a treatment for very dry skin or dehydrated skin, the CRT/ampule may also comprise botanical (essential) oils such as Vevain oil, rosewood oil, lemon oil, and/or grapefruit oil, but in therapeutic regimens it is preferred not to have these botanical oils. When these oils are present, the CRT/ampule is used in a maintenance regimen when the skin is intact and the epidermis is not broken.

Treatment regimens are herein provided using the compositions and formulations as described above. Various different combinations of the use of a healing bar, occlusive dressing, healing cream 1 or 2 and CRT/ampule of the invention are useful in treating various conditions as described below, but is not limited treating these conditions.

Treatment Regimen for Compromised Skin Barrier (Damaged Epidermis)

A treatment regimen is provided for treating a patient having had an injury or treatment that destroys or damages the epidermis, including, but not limited to, $CO_2$ laser resurfacing treatment, phototherapy, and $2^{nd}$ or $3^{rd}$ degree burns. Laser resurfacing treatments, commonly performed with a $CO_2$ laser effectively remove destroy the epidermis with $2^{nd}$ or $3^{rd}$ degree burns. Phototherapy or Photodynamic therapy "PDT" is currently being used at a treatment for basal cell carcinoma (BCC). It is also being used for other conditions in which there is rapid proliferation of cells. Some of those include: Actinic cheilitis, Viral warts, Cutaneous T-cell lymphoma. Kaposi's sarcoma, Extramammary Paget's disease, Psoriasis, Cutaneous vascular malformations and is also used in Hair epilation. Photodynamic therapy (PDT) involves a non-invasive oxygen-dependent phototoxic reaction that can be used for multiple lesions at one time. The photosensitizer can be given intravenously or can be applied to the target lesion topically. It is selectively localized in the target tissue and illuminated with visible light, resulting in photo damage and subsequent cell death.

A treatment regimen for a damaged or destroyed epidermis comprises, or consists essentially of or consists of the use of an occlusive dressing, a CRT/ampule, and a healing cream as described herein. The occlusive dressing is used on day 1-3 post procedure or injury. About 1-2 mm of the occlusive dressing is applied over the entire area of the procedure or injury. This is performed 3-4 times a day.

On days 3-10 post procedure, a CRT/ampule as described herein is applied 3-4 times a day. The patient applies to the area with light taps and then gently and evenly spreads the CRT/ampule. On day 3 after the CRT/ampule treatment, the patient applies the occlusive dressing as described above. On days 4-10, after the CRT/ampule step, the patent applies a healing cream 1 or healing cream 2. The healing cream 1 or 2 is applied evenly over the entire area of the procedure or injury and this is performed 3-4 times a day. More frequent applications of the occlusive dressing or healing cream can be performed if desired (e.g. to alleviate pain and/or inflammation).

The regimen may be continued for 4-8 weeks and thereafter a weekly/daily maintenance program may be used following the treatment regimen. The maintenance program comprises cleansing, preferably with a healing bar of the invention, application of the CRT/ampule once a day and application of the healing cream. Preferably the cleansing and the healing cream are used twice a day.

In other similar regimen, the occlusive dressing is used for about 8 days (3-4 times daily) with no other healing formulation. If more applications of occlusive dressing are desired they may be used. After the 7 or 8 days, in addition to continued use of the occlusive dressing, a healing cream of the invention (e.g. healing cream formulation 1 or 2) is used for about 7 days (with 3-4 times daily application or more as needed (e.g. for pain and inflammation reduction). On day 14, in addition to the occlusive dressing and healing cream, the CRT/ampule is applied following the occlusive dressing.

A maintenance program may be used following the treatment regimen described above for preferably at least once a day. The maintenance program comprises cleansing, preferably with a healing bar of the invention, application of the CRT/ampule once a day and application of the healing cream. Preferably the cleansing and the healing cream are used twice a day.

The invention also provides a method of treating a patient having a compromised skin barrier (damaged epidermis), including a $2^{nd}$ or $3^{rd}$ degree burn, the method comprising administering a treatment regimen as described above to the patient. By treating it is meant that the condition is improved, that is there may be a reduction in pain, reduction of erythema, and reduction of inflammation. The reductions may occur faster and may be "stronger" or "better" as compared to commonly used treatments, such as the use of Aquaphor®. An improved skin texture and improved skin healing maybe seen as compared to other known and commonly used treatments.

Treatment Regimen for Radiodermatitis

A treatment regimen for a treating radiodermatitis comprises, or consists essentially of, or consists of the use of a healing bar, a CRT/ampule, an occlusive dressing and a healing cream as described herein. The first step in the regimen is to cleanse the area with a healing bar of the invention. In the morning and evening the patient is to dampen the skin with warm water and spread the healing bar gently in a circular motion over the affected area. A thin creamy layer of the healing bar "lather" is left on the skin for 1-2 minutes and then is rinsed thoroughly with lukewarm water.

The second step in the regimen, in the morning is to apply a CRT/ampule of the invention and allow it to absorb into the skin. It may be desirable to instead of the CRT/ampule, apply the occlusive dressing, but for convenience sake, patients may prefer to in the morning use the CRT/ampule and in the evening use the occlusive dressing. In the evening, the second step is to apply and lightly rub in a thin layer of an occlusive dressing of the invention to the affected area. Enough of the occlusive dressing product should be applied so that a "shine" of the product can be seen over the area of the most severe radiation induced dermatitis. The application of the occlusive dressing can be performed throughout the day as needed (e.g. for reduction of pain).

Once the skin is in the process of repair and shows signs of healing, then the CRT/ampule may replace the use of the occlusive dressing and may be used once a day.

After both the morning and the evening second steps, the regimen continues with a healing cream of the invention. A healing cream 1 or 2 is applied in a thin layer over the entire area treated in step 2. Enough should be applied (typically 1 to 2 pumps from the bottle) so that one can still see the cream on the surface of the area being treated. The cream is allowed to be absorbed for several moments and then the rest of the cream is gently rubbed over the primary area and then feathered out about 3-4 times per day or more as needed for alleviation of dryness, pain and/or inflammation. The regimen continues until the affected area is healed, which is usually within 3-4 weeks after the last radiation treatment. It may be desirable to begin the treatment during the course of the radiation and continue on after the radiation treatment is finished until the area is healed and continue with the regimen for 4-6 months after radiation was terminated.

After the healing has been achieved it is desirable to continue with a maintenance program. The maintenance program comprises cleansing, preferably with a healing bar of the invention, application of the CRT/ampule once a day and application of the healing cream. Preferably the cleansing and the healing cream are used twice a day.

The present invention also provides a method of treating radiodermatitis. A method for treating radiodermatitis comprises, or consists essentially of or consists of administering the treatment regimen described above a patient in need thereof.

Treatment Regimen for Ectopic Dermatitis, Psoriasis, Eczema

A treatment regimen is provided for treating a patient having ectopic dermatitis, psoriasis, eczema that comprises, or consists essentially of, or consists of the use of a healing bar, an occlusive dressing and a healing cream as described herein. The first step in the regimen is to cleanse the area with a healing bar of the invention. In the morning and evening the patient is to dampen the skin with warm water and spread the healing bar gently in a circular motion over the affected area. A thin creamy layer of the healing bar "lather" is left on the skin for 1-2 minutes and then is rinsed thoroughly with lukewarm water.

The second step is to apply and lightly rub in a thin layer of an occlusive dressing of the invention to the affected area, starting in the central area of the ectopic dermatitis, psoriasis, or eczema and feathering out to the periphery of the affected area. Enough of the occlusive dressing product should be applied so that a "shine" of the product can be seen over the area of the most severe outbreak. This should be performed 3-4 times per day or as needed.

The regimen optionally provides for the application of the CRT/ampule after the second step before the application of the healing cream 1 or 2 mentioned below. In this case, the CRT/ampule is applied and allowed to absorb into the skin before proceeding to the application of a healing cream 1 or 2. This option is particularly useful in the treatment of psoriasis. The CRT is only applied once a day but the healing cream should be applied 3-4 times per day or more as needed.

A healing cream 1 or 2 is applied in a thin layer over the entire area treated in step 2. Enough should be applied so that one can still see the cream on the surface of the area being treated. The cream is allowed to be absorbed for several moments and then the rest of the cream is gently rubbed over the primary area and then feathered out. This should be performed 3-4 times per day or as neede.

The regimen continues until the affected area is healed and inflammation has subsided and is under control. For chronic and severe conditions, usually the regimen lasts about 2 month. After the healing regimen, a maintenance program should begin. The maintenance program comprises cleansing, preferably with a healing bar of the invention, application of the CRT/ampule once a day and application of the healing cream. Preferably the cleansing and the healing cream are used twice a day.

There is provided a method of treating a patient having ectopic dermatitis, psoriasis, or eczema that comprises, or consists essentially of, or consists of administering to a patient in need thereof the treatment regimen as described above.

Treatment Regimen for Pediatric Eczema

The treatment regimen for pediatric eczema is similar to the treatment for ectopic dermatitis, psoriasis, eczema described above, but preferably healing cream 1 is used instead healing cream 2. The regimen progresses as needed, but results have been seen in as little as two to four weeks. Thereafter, a maintenance program should be instituted. The maintenance program comprises cleansing, preferably with a healing bar of the invention, application of the CRT/ampule once a day and application of the healing cream. Preferably the cleansing and the healing cream are used twice a day.

There is provided a method of treating pediatric eczema in a pediatric patient that comprises, or consists essentially of, or consists of administering to the patient in need thereof the pediatric eczema treatment regimen as described above.

Treatment Regimen for Rosacea

A treatment regimen is provided for treating a patient having rosacea that comprises, or consists essentially of, or consists of use of a healing bar, an occlusive dressing, a CRT/ampule and a healing cream as described herein. The first step in the regimen is to cleanse the area with a healing bar of the invention. In the morning and evening the patient is to dampen the skin with warm water and spread the healing bar gently in a circular motion over the affected area. A thin creamy layer of the healing bar "lather" is left on the skin for 1-2 minutes and then is rinsed thoroughly with lukewarm water.

In the morning, it is preferable to apply and lightly rub in a thin layer of an occlusive dressing of the invention to the affected area, starting in the central area of the rosacea and feathering out to the periphery of the affected area. Enough of the occlusive dressing should be applied so that a "shine" of the product can be seen over the area of the most severe outbreak. This can be done once a day or more as needed. If the patient can not apply the occlusive dressing in the morning, the patient may do this procedure in the evening and in the morning instead use a CRT/ampule of the invention. The CRT/ampule is applied and allowed to absorb into the skin before proceeding to the application of the healing cream 1 or 2.

After the morning and the evening treatment as well as throughout the day, a healing cream of the invention is applied. A healing cream 1 or 2 is applied in a thin layer over the entire area treated in step 2. Enough should be applied so that one can still see the cream on the surface of the area being treated. The cream is allowed to be absorbed for several moments and then the rest of the cream is gently rubbed over the primary area and then feathered out. The healing cream can be applied 3-4 times per day, or more as needed to alleviate conditions. If the patient experiences burning or tingling the healing cream can be applied first and the CRT/ampule can be applied.

After the rosacea has cleared, the patient should being a maintenance program. The maintenance program is similar to the treatment regimen discussed but no occlusive dressing is used, and instead a CRT/ampule of the invention is applied. The patient should continue the use of a healing bar and healing cream, at least once or twice a day.

There is provided a method of treating a patient having rosacea that comprises, or consists essentially of, or consists of administering to the patient in need thereof the rosacea treatment regimen as described above.

Treatment Regimen for Acne, Warts, and Blisters

A treatment regimen is provided for treating a patient having acne, warts, or blisters that comprises, or consists essentially of, or consists of the use of a healing bar, an occlusive dressing and a healing cream as described herein. The first step in the regimen is to cleanse the area with a healing bar of the invention. In the morning and evening the patient is to dampen the skin with warm water and spread the healing bar gently in a circular motion over the affected area. A thin creamy layer of the healing bar "lather" is left on the skin for 1-2 minutes and then is rinsed thoroughly with lukewarm water. The healing bar may preferably contain *cannabis* oil 0.05-1.5%.

The second step is to apply and lightly rub in a thin layer of an occlusive dressing of the invention containing *cannabis* oil at 0.5-4% (as described herein) to the affected area. Enough of the occlusive dressing product should be applied so that a "shine" of the product can be seen over the area of concern.

A healing cream 1 or 2 is applied in a thin layer over the entire area treated in step 2. Enough should be applied so that one can still see the cream on the surface of the area being treated. The cream is allowed to be absorbed for several moments and then the rest of the cream is gently rubbed over the primary area and then feathered out. The regimen continues until the affected area is healed (acne is reduced or gone, blisters are healed or warts have disappeared).

A maintenance regimen to prevent further breakouts of acne or warts is preferred. The maintenance program comprises cleansing, preferably with a healing bar of the invention, application of the CRT/ampule once a day and application of the healing cream. Preferably the cleansing and the healing cream are used twice a day.

There is provided a method of treating a patient having acne, blisters or warts that comprises, or consists essentially of, or consists of administering to the patient in need thereof the acne, warts or blister treatment regimen as described above.

Treatment Regimen for Canker Sores (in the Mouth)

In the regimen for treating canker sores, the occlusive dressing comprising *cannabis* oil at 0.5-4% as described herein is applied 3-4 times per day to the canker soil. Because the ingredients are natural and safe, it is safe to apply the occlusive dressing in the mouth. This is performed 3-4 times per day or as needed to reduce the pain and or inflammation caused by the canker sore. A dot of occlusive dressing is applied with a cotton swab on the canker sore and repeated 3-4 times per day.

There is provided a method of treating a patient having a canker sore in the mouth that comprises, or consists essentially of, or consists of administering to the patient in need thereof the canker sore treatment regimen as described above.

Treatment Regimen for Xerosis Cutis

Xerosis cutis is the medical term for abnormally dry skin. Xerosis cutis is worse during the cold winter months when the air is very dry (low humidity). Older people are more susceptible to developing the condition than younger people. It is a very painful condition and symptoms of xerosis cutis include: skin that is dry, itchy, and scaly, especially on the arms and legs, skin that feels tight, especially after bathing, white, flaky skin, red or pink irritated skin, and fine cracks on the skin.

A treatment regimen is provided for treating a patient having Xerosis cutis that comprises, or consists essentially of, or consists of the use of a healing cream as described herein. Optionally, the patient may use the healing bar as described herein to wash. The healing cream is applied as often as needed too alleviate the symptoms and to reduce discomfort and pain.

It may also be desired to use an occlusive dressing when the skin has becomes so dry that it cracks and an open wound is created, and is applied 1 to 2 times a day or more as needed.

There is provided a method of treating a patient having Xerosis cutis that comprises, or consists essentially of, or consists of administering to the patient in need thereof the Xerosis cutis treatment regimen as described above.

Treatment Regimen for Patients Post Plastic Surgery and Post Injection of Fillers A treatment regimen is provided for treating a patient post plastic surgery and post injection of fillers. The first step in the regimen is to cleanse the area with a healing bar of the invention. In the morning and evening the patient is to dampen the skin with warm water and spread the healing bar gently in a circular motion over the affected area. A thin creamy layer of the healing bar "lather" is left on the skin for 1-2 minutes and then is rinsed thoroughly with lukewarm water.

The second step of the regimen involves the application of the CRT/ampule. In this case, the CRT/ampule is applied (1 time per day) and allowed to absorb into the skin before proceeding to the application of a healing cream 1 or 2. The healing cream is applied 3-4 times per day or as needed.

A healing cream 1 or 2 is applied in a thin layer over the entire area treated in step 2. Enough should be applied so that one can still see the cream on the surface of the area being treated. The cream is allowed to be absorbed for several moments and then the rest of the cream is gently rubbed over the primary area and then feathered out. This should be performed 3-4 times per day or as needed.

The regimen continues until the affected area is healed and inflammation has subsided and is under control. The regimen enhances/speeds recovery and reduces the appearance or formation of scars.

A maintenance program can be used after the treatment regimen and comprises cleansing, preferably with a healing bar of the invention, application of the CRT/ampule once a day and application of the healing cream. Preferably the cleansing and the healing cream are used twice a day.

There is also provided a method of treating a patient having undergone plastic surgery or received an injection of a filler. The method comprises, or consists essentially of, or consists of administering to the patient in need thereof the treatment regimen as described above.

Methods of Treatment of use of Compositions to make a Medicament to Treat Patients.

The invention provides use of the various compositions and regimens described herein above to treat various conditions. The methods of treatment involve administering the described regimens to a patient in need thereof. Regimens described herein can promote healing of the condition and is safe, can be used on children and does not cause allergic reactions or unwanted side effects. By treating it is meant that the condition is improved, that is there may be a reduction in pain, reduction of erythema, and reduction of inflammation. The reductions may occur faster and may be "stronger" or "better" as compared to commonly used treatments, such as the use of Aquaphor®. An improved skin texture and improved skin healing maybe seen as compared to other known and commonly used treatments.

With the compositions of the invention and the various formulations, a reduction of pain and discomfort, as well as a reduction itchiness and a substantial skin calming effect has been seen in patient with the conditions described herein.

Kits

The present invention also provides kits containing different compositions of the invention described herein. For instance, there is provided a kit comprising a healing bar, occlusive dressing, healing cream and instructions for use (for example, proving instructions for use of the individual products as well as for the treatment regimen for treating eczema or ectopic dermatitis).

There is also provided a kit comprising a healing bar, CRT/ampule, occlusive dressing and healing cream and instructions for use (for example, proving instructions for use of the individual products as well as for the treatment regimen for treating radiodermatitis or psoriasis).

There is also provided a kit comprising occlusive dressing, CRT/ampule and healing cream and instructions for use (for example, proving instructions for use of the individual products as well as for the treatment regimen for treating conditions involving burns or damage or destruction to the epidermis, such as from but not limited to, $CO_2$ laser resurfacing and PDT treatments).

EXAMPLES

Example 1: Rosacea

A patient suffering for rosacea for years utilized a CRT/ampule and healing cream of the invention twice daily and saw an improvement and complete reduction of redness within less than two months.

Example 2: $CO_2$ Laser Resurfacing Patients

At the initial visit (Day-14 to Day 0), those subjects meeting the inclusion/exclusion criteria are entered into the study. Prior to receiving any study treatment, photographs of the subject's treatment area will be taken. All photographs (using the Canfield 3D Vectra system) are mandatory and may be used for research and/or commercial use. Investigator assessment of pre-treatment photographs using the 9-point Fitzpatrick-Goldman Classification of Wrinkling and Degree of Elastosis Scale1 will also be performed. A topical anesthetic cream will be applied to the face for 30 minutes. IV sedation and local nerve blocks will be performed as needed. The subjects will then receive fractionated $CO_2$ laser resurfacing to the face (Day 0). Initial screening visit and treatment may be performed on the same day. Women of childbearing potential will have a urine pregnancy test performed prior to treatment. Immediately following the treatment, postoperative gel randomized to the face (regimen of the invention or placebo) will be applied. Randomization will be performed by an unblinded coordinator with a randomly generated table via coin flip in a 3 to 1 fashion. Subjects will be queried after procedure prior to gel application and at every follow up visit about pain, itching, tightness, oozing and crusting if experienced and duration.

At the third visit (Day 1), the investigator will assess Face erythema, edema, exudation, crusting, & percentage of healing and will query the subject for self-assessment of Face discomfort, itching, tightness, oozing and crusting. The patient will cleanse their Face with Cetaphil cleanser, photographs of the subject's treatment area will be taken and then a blinded coordinator will apply the appropriate study gel and review the post laser resurfacing skin care instructions.

At the fourth visit (Day 3), the investigator will assess Face erythema, edema, exudation, crusting, & percentage of healing and will query the subject for self-assessment of Face discomfort, itching, tightness, oozing and crusting. The patient will cleanse their Face with Cetaphil cleanser, photographs of the subject's treatment area will be taken and then a blinded coordinator will apply the appropriate study gel and review the post laser resurfacing skin care instructions.

At the fifth visit (Day 7), the investigator will assess Face erythema, edema, exudation, crusting, & percentage of healing and will query the subject for self-assessment of Face discomfort, itching, tightness, oozing and crusting. The patient will cleanse their Face with Cetaphil cleanser, photographs of the subject's treatment area will be taken and then a blinded coordinator will apply the appropriate study gel and review the post laser resurfacing skin care instructions.

At the sixth visit (Day 10), the investigator will assess Face erythema, edema, exudation, crusting, & percentage of healing and will query the subject for self-assessment of Face discomfort, itching, tightness, oozing and crusting. The investigator will assess photographs using the 9-point Fitzpatrick-Goldman Classification of Wrinkling and Degree of Elastosis Scale. Photographs of the subject's treatment area will be taken and the Coordinator will also review post laser resurfacing skin care instructions to ensure they were followed.

At the seventh visit (Day 14), the investigator will assess Face erythema, edema, exudation, crusting. & percentage of healing and will query the subject for self-assessment of Face discomfort, itching, tightness, oozing and crusting. The investigator will assess photographs using the 9-point Fitzpatrick-Goldman Classification of Wrinkling and Degree of Elastosis Scale. Photographs of the subject's treatment area will be taken and the Coordinator will also review post laser resurfacing skin care instructions to ensure they were followed.

At the eighth visit (Day 30), the investigator assess Face erythema, edema, exudation, crusting, & percentage of healing and will query the subject for self-assessment of Face discomfort, itching, tightness, oozing and crusting. The investigator will assess photographs using the 9-point Fitzpatrick-Goldman Classification of Wrinkling and Degree of Elastosis Scale. Photographs of the subject's treatment area will be taken and the Coordinator will also review post laser resurfacing skin care instructions to ensure they were followed.

During the course of the study, if a subject experiences intolerable irritation due to a study treatment, the treatment gel may be temporarily altered at the investigator's discretion. Any changes in the treatment gel must be noted in the subject's records.

Efficacy will be assessed by evaluating magnitude and duration of all investigator assessments and subject ratings including time to resolution of individual signs and symptoms. Subject satisfaction related to healing time and skin quality ratings will be analyzed on a categorical basis. Safety will be assessed by evaluating reports of discomfort and any adverse medical events reported.

The patients received either a placebo gel (Aquaphor®) (active ingredient—petrolatum 14%) or a treatment regimen as follows: An occlusive dressing as described herein was used on day 1-3 post procedure or injury. About 1-2 mm of the occlusive dressing was applied over the entire area of the procedure or injury. This was performed 3-4 times per day.

On days 3-10 post procedure, a CRT/ampule as described herein was applied 3-4 times per day. The patient applied the CRT/ampule to the area with light taps and then gently and evenly spread the CRT/ampule. On day 3 after the CRT/ampule treatment, the patient applied the CRT/ampule as described above. On days 4-10, after the CRT/ampule step, the patent applied a healing cream 1. The healing cream 1 was applied event over the entire area of the procedure and this was done 3-4 times per day.

The patients experienced an improved healing over that of the placebo patients. They did not experience any adverse effects and had no allergic reactions. A reduction in pain, reduction of erythema, and reduction of inflammation was observed. There was an improved skin texture and improved skin healing in the patients using the regimen of the invention. The patients reported that the products used in the regimen were soothing, easy and pleasant to use.

Example 3: Eczema and Pediatric Eczema

Patents with eczema or pediatric patients with eczema are enrolled in a study. The test regimen they will receive is as described herein above. Clearing of eczema was seen in pediatric patients as quickly as two to four weeks.

Example 4: Ectopic Dermatitis

Patents with ectopic dermatitis are enrolled in a study. The test regimen they will receive is as described herein above. The study is carried out for about 6-8 weeks. Healing of the skin cells and reduction of symptoms is expected to be seen between 2-5 weeks.

Example 5: Psoriasis

Patents with psoriasis are enrolled in this study. The test regimen they will receive is as described herein above. Cessation of redness can be seen in as little as 3-4 weeks.

Example 6: Radiodermatitis

Patients suffering from radiodermatitis are enrolled in this study. The test regimen they will receive is as described herein above. Improvements are expected to be seen in 1-2 weeks after the radiation treatment. Reduced redness and rash is expected to be seen.

Example 7: Acne, Blisters, and/or Warts

Patients suffering from acne or warts will be enrolled in the study. The test regimen they will receive is as described herein above. Improvement in acne and healing of blisters is expected be seen in a week to 10 days. It is expected that warts will disappear from about 3 weeks to 3 months.

Example 8: Canker Sores in the Mouth

Patients suffering from a canker sore are enrolled in the study. The test regimen they will receive is as described herein above. The canker sores were cleared in 3-5 days.

The invention claimed is:

1. A healing composition useful in the healing or treatment of skin conditions wherein the composition comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% of the composition, the *rosa canina* oil comprises 2-5% of the composition, the inula viscosa oleoresin comprises 0.05-1.5% of the composition; and the *citrus medica* vulgaris etrog oil, or an extract thereof comprises 0.1-2% of the composition.

2. The composition of claim 1 formulated into a solid composition healing bar.

3. The composition of claim 1 further comprising, *olea europea* (olive oil) present at 1-3% of the composition, *butyrspermum parkii* butter (shea butter) present at 2-5% of the composition, *aloe barbadensis* gel present at 1.5-3.5% of the composition, sulfur present at 0.75-4% of the composition, colloidal silver present at 0.5-3% of the composition, *achillea millefolium* (common yarrow) present at 0.5-2% of the composition; *equisetum arvense* (horsetail) present at 0.5-2% of the composition, chamomile flower extract present at 1-3% of the composition and zinc present at 0.5-1.75% of the composition.

4. The composition of claim 3 further comprising *cannabis* oil present at 0.05-1.5% of the composition.

5. A healing composition useful in the healing or treatment of skin conditions formulated into a balm/occlusive dressing wherein the composition comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition.

6. The composition of claim 5 further comprising cera alba (beeswax) at 15-25% of the composition and vegetable lanolin (omega 3) as its base.

7. The composition of claim 5 further comprising *cannabis* oil at 2-4%.

8. A healing composition useful in the healing or treatment of skin conditions formulated into a healing cream wherein the composition comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 2-5% of the composition, the *rosa canina* oil comprises 2-4% of the composition, the inula viscosa oleoresin comprises 0.03-0.2% of the composition; and the *citrus medica* vulgaris etrog oil, or an extract thereof comprises 0.1-2% of the composition, and further comprises *butyrspermum parkii* butter (shea butter) comprising 3.0-6.0% of the composition, cera alba (bees wax) at 3.0-6.0% of the composition, *aloe barbadensis* leaf juice at 1.0-1.6% of the composition, *Vitis vinifera* seed oil (grape seed oil) at 2.0-4.0% of the composition, *Daucus carota sativa* root extract (wild carrot extract in olive oil) at 2.0-5.0% of the composition.

9. A healing composition useful in the healing or treatment of skin conditions wherein the composition comprises punica granatum oil (pomegranate seed oil) having about 80% punicic acid, *rosa canina* fruit oil, inula viscosa oleoresin (or extract thereof), and *citrus medica* vulgaris etrog oil, or an extract thereof, wherein the punica granatum oil is unoxidized, wherein the punica granatum oil comprises 3-6% of the composition, the *rosa canina* oil comprises 2-5% of the composition, the inula viscosa oleoresin comprises 0.05-1.5% of the composition; and the *citrus medica* vulgaris etrog oil, or an extract thereof comprises 1-5% of the composition and further comprises *Salix alba* bark extract (white willow bark) comprising 1.0-3.0% of the composition, and chamomile flower extract comprising 1.5 to 3.0% of the composition.

10. The composition of claim 9 further comprising *butyrspermum parkii* butter (shea butter) comprising 2.5-5.0 of the composition, cera alba (bees wax) comprising 2.0-5.0% of the composition, *aloe barbadensis* leaf juice comprising 1.0-3.0% of the composition, and *Daucus carota sativa* root extract (wild carrot extract in olive oil) comprising 3.0-6.0% of the composition.

11. A treatment regimen for treating a patient having had an injury or treatment that destroys or damages the epidermis, the regimen comprising the use of an occlusive dressing, a concentrated repair treatment (CRT) comprising punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition, and a healing cream, wherein the regimen comprises:

a) on days 1-3 post procedure or injury, applying the occlusive dressing at about 1-2 mm thick over the entire area of the injury, 3-4 times a day;

b) on days 3-10 post procedure, applying CRT 1 time a day over the entire area of the injury;

c) on day 3 after the CRT treatment, applying the occlusive dressing wherein the occlusive dressing is applied 3-4 times a day;

d) on days 4-10, after the CRT step, applying a healing cream evenly over the entire area of the injury, 3-4 times a day, wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition, and wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition.

12. A treatment regimen for treating a patient having had an injury or treatment that destroys or damages the epidermis, the regimen comprising the use of an occlusive dressing, a concentrated repair treatment (CRT), and a healing cream, wherein the regimen comprises:

a) for the first 7-8 days following the injury or treatment, applying the occlusive dressing 3-4 times daily;

b) after the first 7 or 8 days, in addition to continued use of the occlusive dressing, applying a healing cream for about 7 days, 3-4 times daily;

c) on about day 14, in addition to the occlusive dressing and healing cream, applying the CRT once a day following the application of the occlusive dressing, wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition, and wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and wherein the concentrated repair treatment (CRT) comprises punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition.

13. A treatment regimen for a treating radiodermatitis comprising, the use of a healing bar, a concentrated repair treatment (CRT), an occlusive dressing, and a healing cream, the regimen comprising:
  a) cleansing the area affected by radiodermatitis with the healing bar to form a lather and allowing the healing bar lather to remain on the skin for 1-2 minutes, and rinsing thoroughly;
  b) in the morning, applying the CRT or the occlusive dressing to the affected area and allowing it to absorb into the skin,
  c) in the evening, applying the occlusive dressing to the area affected by radiodermatitis;
  d) after both the morning and the evening steps of applying the CRT in the morning and the occlusive dressing in the evening, applying the healing cream over the area affected by radiodermatitis about 3-4 times per day,
  wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition, and
  wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and
  wherein the healing bar comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar,
  wherein the concentrated repair treatment (CRT) comprises punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition.

14. A treatment regimen for treating a patient having atopic dermatitis, psoriasis, or eczema that uses a healing bar, an occlusive dressing, and a healing cream, the regimen comprising:
  a) cleaning the skin in the morning and evening with the healing bar to form a lather, and allowing a layer of the healing bar lather to remain on the skin for about 1-2 minutes and then is rinsing thoroughly;
  b) applying a thin layer of the occlusive dressing to an area of the skin affected by ectopic dermatitis, psoriasis or eczema, 3-4 times per day;
  c) optionally apply a CRT to the area of the skin affected by ectopic dermatitis, psoriasis or eczema after the second step, 1 time per day;
  d) applying the healing cream over the area of the skin affected by ectopic dermatitis, psoriasis or eczema, 3-4 times per day,
  wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition, and
  wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and
  wherein the healing bar comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar,
  wherein the concentrated repair treatment (CRT) comprises punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition.

15. A treatment regimen for treating a patient having rosacea that uses a healing bar, an occlusive dressing, a concentrated repair treatment (CRT), and a healing cream, the regimen comprising:
  a) cleaning the skin in the morning and evening with the healing bar to form a lather and allowing a layer of the healing bar lather to remain on the skin for about 1-2 minutes and then rinsing thoroughly;
  b) in the morning, applying a thin layer of the occlusive dressing or CRT to the area affected by rosacea;
  c) in the evening applying a thin layer of the occlusive dressing if the CRT was applied in the morning or if the occlusive dressing was applied in the morning, applying the CRT to the area affected by rosacea;

c) applying the healing cream over the entire area affected by rosacea after the morning and evening steps and applying 3-4 times through-out the day, wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition, and wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and wherein the healing bar comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar, wherein the concentrated repair treatment (CRT) comprises punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition.

16. A treatment regimen for treating a patient having acne, warts, or blisters comprising the use of a healing bar, an occlusive dressing, and a healing cream, the regimen comprising:
a) cleaning the skin in the morning and evening with the healing bar to form a lather and allowing a layer of the healing bar lather to remain on the skin for about 1-2 minutes and then rinsing thoroughly, wherein the healing bar further contains *cannabis* oil 0.05-1.5%;
b) applying a layer of the occlusive dressing to the area affected by acne, warts or blisters 3-4 times per day, wherein the occlusive dressing further contains *cannabis* oil at 0.5 to 4%; and
c) applying the healing cream over the affected area 3-4 times per day, wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition, and wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and wherein the healing bar comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar.

17. A treatment regimen for healing canker sores (in the mouth) comprising the use an occlusive dressing as set forth in claim 5, the regimen comprising:
a) applying the occlusive dressing 3-4 times per day to the canker sore to treat the canker sore.

18. A treatment regimen for treating patients with Xerosis cutis, comprising the use of the occlusive dressing as set forth in claim 5, a healing cream, and a healing bar, the regimen comprising:
a) applying the healing cream to skin; and optionally,
b) applying the occlusive dressing when the skin has cracked and an open wound is created; and optionally,
c) washing the skin with the healing bar in the morning and evening, wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and wherein the healing bar comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar.

19. A treatment regimen for patients post plastic surgery and post injection of fillers, comprising the use a healing bar, a concentrated repair treatment (CRT), and a healing cream, the regimen comprising:
a) cleaning the skin in the morning and evening with the healing bar to form a lather and allowing a layer of the healing bar lather to remain on the skin for about 1-2 minutes and then rinsing thoroughly;

b) applying the CRT to an area affected by the plastic surgery or by injection of the fillers 1 time per day;

c) applying the healing cream in a thin layer over the area affected by the plastic surgery or by injection of the fillers 3-4 times per day, wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and wherein the healing bar comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar, wherein the concentrated repair treatment (CRT) comprises punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition.

20. A kit comprising a healing bar, a CRT a healing cream, and instructions for use, wherein the healing cream comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition, and wherein the healing bar comprises formulated comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 3-6% or 2-5% of the composition, the *rosa canina* oil comprises 2-5% or 2-4% of the composition, the inula viscosa oleoresin comprises 0.5-1.5% or 0.03-0.2% of the composition; and the *citrus medica* vulgaris etrog oil, or an extract thereof comprises 0.1-2% or 1-5% of the composition formulated into a solid healing bar, wherein the concentrated repair treatment (CRT) comprises punica granatum oil (pomegranate seed oil) having about 80% punicic acid present at 45-65% of the CRT composition; Calendula infused Jojoba oil present at 15-25% of the CRT composition, and *rosa canina* oil present at 20-35% of the CRT composition.

21. The kit of claim 20 wherein the kit further comprises an occlusive dressing wherein the occlusive dressing comprises punica granatum oil (pomegranate seed oil) having about 80% punicic acid, *rosa canina* fruit oil, inula viscosa oleoresin (or extract thereof), wherein the punica granatum oil is unoxidized, wherein the punica granatum oil comprises 5-9% of the composition, the *rosa canina* oil comprises 4-8% of the composition, the inula viscosa oleoresin comprises 0.05-1.5% of the composition; and the *citrus medica* vulgaris etrog oil, or an extract thereof comprises 0.1-2% of the composition.

22. The healing composition of claim 1 formulated into a healing cream.

23. The healing composition of claim 3 formulated into a healing cream.

24. The healing composition of claim 9 formulated into a healing cream.

25. The healing composition of claim 11 formulated into a healing cream.

* * * * *